United States Patent [19]

Okada et al.

[11] Patent Number: 5,247,169

[45] Date of Patent: Sep. 21, 1993

[54] METHOD OF AND AN APPARATUS FOR PICKING UP AN IMAGE OF THE SURFACE OF AN OBJECT TO BE INSPECTED

[75] Inventors: Takao Okada; Katsuyuki Suzuki, both of Ibaraki, Japan

[73] Assignee: Ikegami Tsushinki Co., Ltd., Tokyo, Japan

[21] Appl. No.: 941,787

[22] Filed: Sep. 8, 1992

[30] Foreign Application Priority Data

Sep. 9, 1991 [JP] Japan ................... 3-228078

[51] Int. Cl.[5] .................................. G01J 3/50
[52] U.S. Cl. .................... 250/226; 209/582; 356/407; 356/419
[58] Field of Search ............... 250/226, 216; 209/582, 209/580, 581; 356/419, 416, 407

[56] References Cited

U.S. PATENT DOCUMENTS

| | | | |
|---|---|---|---|
| 3,609,047 | 9/1971 | Marlow | 356/419 |
| 3,980,181 | 9/1976 | Hoover et al. | 356/408 |
| 4,082,188 | 4/1978 | Grimmell et al. | 209/582 |
| 4,143,770 | 3/1979 | Grimmell et al. | 209/580 |
| 4,822,998 | 4/1989 | Yokota et al. | 350/226 |

*Primary Examiner*—David C. Nelms
*Assistant Examiner*—T. Davenport
*Attorney, Agent, or Firm*—Mason, Fenwick & Lawrence

[57] ABSTRACT

An object to be inspected is, for example, a medical capsule having differently colored surface areas. A beam splitter divides light reflected by the surface of the object into two parts. Each of the divided parts of the light is passed through an optical filter whose transmission wavelength range is set according to the colors of the object, to adjust the quantity of transmitted light from a high-brightness part of the object surface and the quantity of transmitted light from a low-brightness part of the object surface to a reference level. Image pick-up elements pick up images of the object surface according to the divided parts of the light and provide image signals. One of the image signals is selected and provided outside. Unlike a prior art that adjusts levels of signals by amplifying the signals according to brightness of an inspected object, the method and apparatus of the invention do not involve amplification. The invention, therefore, never amplifies noise components to cause errors in inspection, thereby improving inspection accuracy.

10 Claims, 4 Drawing Sheets

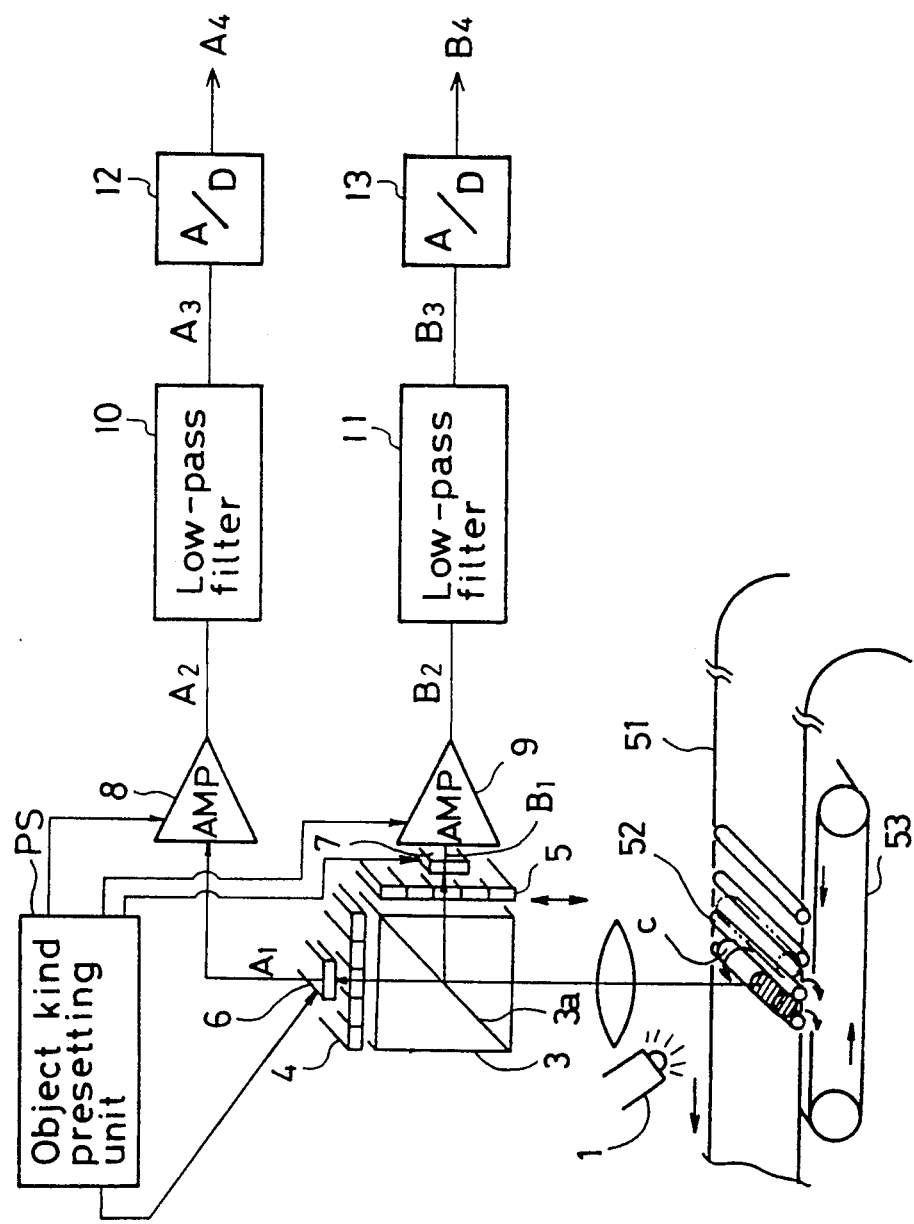

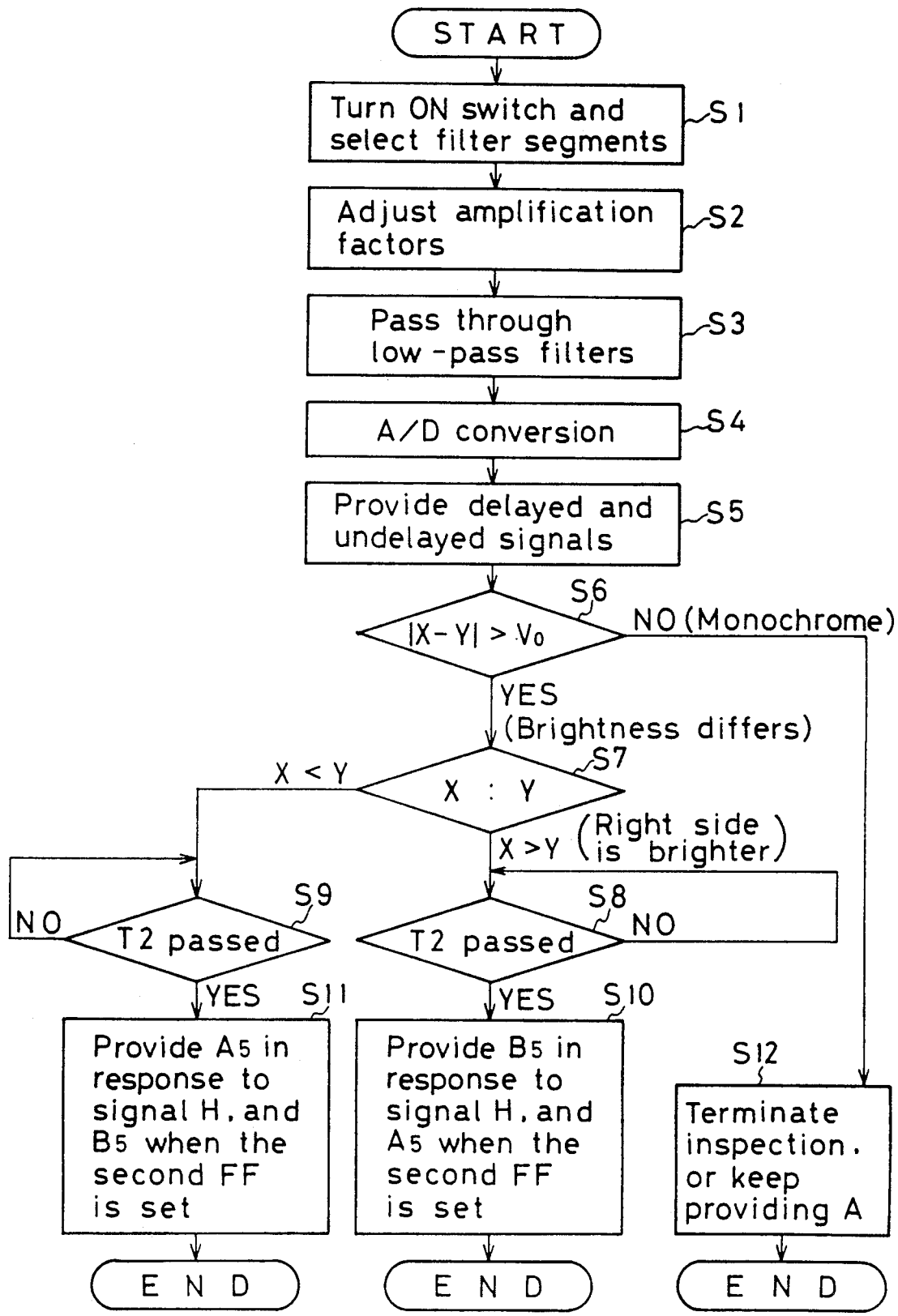

METHOD OF AND AN APPARATUS FOR PICKING UP AN IMAGE OF THE SURFACE OF AN OBJECT TO BE INSPECTED

BACKGROUND OF THE INVENTION

1. Field of the Invention

The present invention relates to a method of and an apparatus for picking up an image of the surface of an object such as a medical capsule to inspect the surface, and particularly, to a technique of accurately inspecting the surface of an object colored with different colors and brightness.

2. Description of the Related Art

Stains, flaws, printing defects, etc., on the surface of a small object such as a medical capsule have usually been inspected by human eyes. Cameras are recently used for such inspection, to improve inspection efficiency and accuracy and to automate the inspection.

Each medical capsule generally comprises two parts colored with different colors and brightness.

To inspect the surface conditions of such capsule, one prior art employs a single camera, which picks up an image of the capsule surface and photoelectrically converts the picked up image into an electrical signal. According to this signal, the prior art checks the surface conditions of the capsule.

During the inspection, high- and low-brightness parts of the capsule provide different base signal levels. If the inspection is carried out based on the same reference level, the difference of signal level may increase the occurrence of errors, to deteriorate inspection accuracy. Accordingly, the prior art employs an amplifier for amplifying the level of a signal from the low-brightness part of the capsule up to the level of a signal from the high-brightness part thereof before carrying out the inspection.

When the signal level of the low-brightness part is amplified, however, noise is also amplified to erroneously indicate that there are stains and flaws.

A CCD image sensor is frequently used as an image pick-up element. When the light quantity of an image formed on the CCD image sensor is too small, noise due to dark current fluctuations and a large amplification factor of an amplifier will greatly influence a result of inspection. On the other hand, when the light quantity of an image formed on the image pick-up element is excessively large, striation noise due to fluctuations in a charge saturation quantity drastically influence a result of inspection.

It is necessary, therefore, to properly set the quantity of light received by the image pick-up element, to improve inspection accuracy and suppress noise. According to the prior art, however, it is very difficult to properly set the quantity of light received by the image pick-up element because the surface of an inspection object colored with different colors and brightness causes a great difference in quantity of light in an image formed on the image pick-up element. This is why the prior art achieves poor inspection accuracy.

An object of the invention is to provide an image signal that causes no erroneous determination due to noise amplification.

Another object of the invention is to enable inspection of the surface of an object by using an image signal that causes no erroneous determination, to thereby improve inspection accuracy.

Still another object of the invention is to pick up an image of the surface of any colored object after equalizing the quantities of light provided by high- and low-brightness parts of the object.

Still another object of the invention is to determine a positional relation between high- and low-brightness parts of the surface of an object, to correctly inspect the surface conditions of the object even if the positional relation is inverted.

Still another object of the invention is to enable inspection of the surface of a monochrome object in the same manner as the surface of a differently colored object.

SUMMARY OF THE INVENTION

In order to accomplish the objects and advantages mentioned above, the invention provides a method of and apparatus for picking up an image of the surface of an object, comprising a light dividing step of and means for dividing light reflected by the object surface into two parts oriented in two directions; a transmitted light quantity adjusting step of and means for transmitting the divided parts of the light through optical filters, respectively, each of the optical filters being set to a specific transmission light wavelength range so that the quantity of light reflected by a high-brightness part of the object surface and passed through a corresponding one of the optical filters is equal to the quantity of light reflected by a low-brightness part of the object surface and passed through the other optical filter; and an image pick-up step of and means for picking up an image from each of the divided parts of the light transmitted through the optical filters.

According to this arrangement, light reflected by the object surface is divided by the light dividing means into two parts oriented in two directions. Each of the divided parts of the light is transmitted through a corresponding one of the optical filters each being set to specific transmission light wavelength range. The transmission light wavelength ranges of the optical filters are set such that the quantity of the light that has been reflected by the high-brightness part of the object surface and transmitted through one of the optical filters is equal to that of the light that has been reflected by the low-brightness part of the object surface and transmitted through the other optical filter.

In this way, the quantities of the transmitted light from the high- and low-brightness parts of the object surface are equalized, and the image pick-up means simultaneously pick up the images of the high- and low-brightness parts of the object at the same positional relations and photoelectrically convert the images into electric image signals.

According to the transmitted light quantity adjusting step and means, the filtering face of each of the optical filters may be divided into a plurality of filter segments having different transmission light wavelength ranges, so that each divided part of light may be transmitted, in each optical filter, through one of the filter segments selected according to the brightness of the object surface.

According to this arrangement, the quantity of light reflected by the high-brightness part of the object surface and transmitted through one of the optical filters will be equal to the quantity of light reflected by the low-brightness part of the object surface and transmitted through the other optical filter, before images of the object surface are picked up. Accordingly, light for illuminating the object may be adjusted so that the image of the object colored with different brightness may be properly picked up.

The method of and apparatus for inspecting an object according to the invention may further comprise a delay output step of or means for delaying one image signal that has been picked up with the quantity of transmitted light from the high-brightness part of the object surface being set to a reference level; and a positional relation determination step of or means for comparing the delayed image signal with the undelayed image signal, to determine a positional relation between the high- and low-brightness parts of the object surface.

According to this arrangement, the image signal obtained with the quantity of transmitted light from the high-brightness part of the object surface being set to the reference level is compared with the delayed image signal for a boundary between the colored parts of the object surface. According to the result of the comparison, a positional relation between the high- and low-brightness parts is determined.

It is possible to include an image signal selection step of or means for switching the two image signals from one to another according to a timing signal generated according to the determined positional relation, and providing an image processing unit with a signal based on the high- or low-brightness part with the transmitted light quantity being set to the reference level.

According to this arrangement, the image signal formed from transmitted light whose quantity is equal to the reference level is selected from among the image signals based on the divided light parts from the high- and low-brightness parts of the object according to the determined positional relation, and provided to the image processing unit. In this way, the image signal is processed after the signal level of the image signal is completely adjusted to the reference level.

The positional relation determination step or means may have a function of providing the image processing unit only with the image signal obtained with the high-brightness part being set to the reference level, if the positional relation decision step or means determines that the object surface is monochrome and involves no brightness difference.

According to this arrangement, an image signal will not be totally saturated even if the surface of the object is monochrome, so that the monochrome object may be inspected in the same manner as in the colored object.

Other objects and features of the present invention will be described hereinafter in detail by way of a preferred embodiment with reference to accompanying drawings.

BRIEF DESCRIPTION OF THE DRAWINGS

FIG. 2 is a flowchart showing operations of the embodiment; and

DESCRIPTION OF THE PREFERRED EMBODIMENTS

A preferred embodiment of the invention will now be explained with reference to the drawings.

Figure 1B:
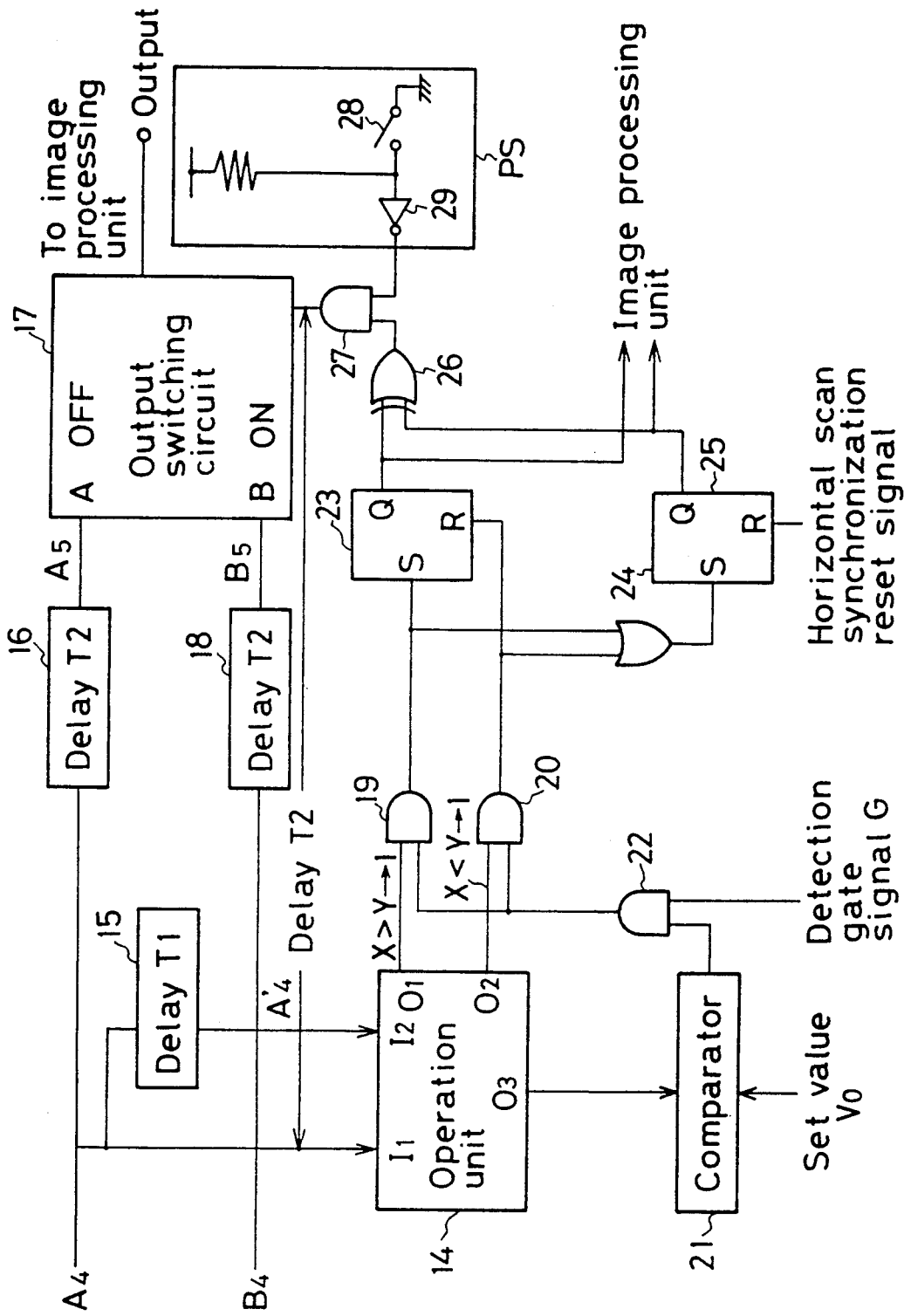
FIGS. 1A and B is a block diagram showing an embodiment of the invention.

In FIG. 1, a medical capsule c is an object to be inspected. A conveyor belt 51 forms a ladder-like closed loop and has spin rollers 52. The capsule c is supported by adjacent ones of the spin rollers 52. The spin rollers 52 are in contact with a spin belt 53, which turns the spin rollers 52. The capsule c is turned around its own axis by the adjacent spin rollers 52 while being transported by the conveyor belt 51. When the capsule c reaches an image pick-up position, an inspection apparatus of the invention picks up an image of the surface of the capsule c and inspects the surface. The capsule c comprises two parts colored with different colors and brightness.

When the capsule c reaches the image pick-up position, a light 1 obliquely illuminates the capsule c. An image pick-up leans 2 disposed above the capsule c collects light reflected by the capsule c. The collected light is made incident to a beam splitter 3 serving as light dividing means. The beam splitter 3 has a half mirror 3a, which divides the incident light into two parts one passing through the half mirror 3a and advancing straight and upwardly, while the other being reflected by the half mirror 3a and advancing horizontally.

Optical filters 4 and 5 serving as transmitted light quantity adjusting means are disposed over the straight and reflected light emitting faces of the beam splitter 3, respectively. The optical filter 4 sets the quantity of transmitted light from a high-brightness part of the surface of the capsule c to a reference level, while the optical filter 5 sets the quantity of transmitted light from a low-brightness part of the surface of the capsule c to a reference level, thereby equalizing the quantities of the transmitted light from the high- and low-brightness parts of the capsule c.

To deal with various kinds of capsules colors with different colors and brightness, the filter surface of each of the optical filters 4 and 5 is divided into a plurality of filter segments having different transmission light wavelength ranges. Each of the optical filters 4 and 5 is moved by a drive mechanism such as a motor (not shown) according to a control signal provided manually or by an object kind presetting unit PS, to select one of the filter segments that is optimum for a brightness combination on the surface of a capsule to be inspected and position it on an optical axis.

CCD line image sensors 6 and 7 are arranged behind and close to the optical filters 4 and 5, respectively. A longitudinal side of each image sensor extends along a longitudinal side of the selected filter segment of the corresponding optical filter. The CCD line image sensors 6 and 7 pick up images from light transmitted through the selected filter segments of the optical filters 4 and 5, respectively.

The CCD line image sensors 6 and 7 thus provide image signals A1 and B1 to amplifiers 8 and 9, which provide signals A2 and B2, respectively. Low-pass filters 10 and 11 remove noise components from the signals A2 and B2 and provide signals A3 and B3, respectively. A/D converters 12 and 13 convert the analog signals A3 and B3 into digital signals A4 and B4, respectively.

The image signal A4 is provided as it is to an input terminal I1 of an operation unit 14. At the same time, the signal A4 is delayed by a delay circuit 15 by a predetermined time T1 and provided as a signal A4' to an input terminal I2 of the operation unit 14. Also, the signal A4 is delayed by a delay circuit 16 by a predetermined time T2 corresponding to one horizontal scan period and provided as a signal A5 to an output switching circuit 17.

The delay circuit 15 serves as delay signal output means.

The other image signal B4 from the A/D converter 13 is delayed by a delay circuit 18 by the predetermined time T2 and provided as a signal B5 to the output switching circuit 17.

The operation unit 14 compares a level X of the undelayed image signal A4 with a level Y of the delayed image signal A4'. If $X > Y$, an output terminal O1 of the operation unit 14 provides a high-level signal to an input terminal of the first AND circuit 19. If $X < Y$, an output terminal O2 of the operation unit 14 provides a high-level signal to an input terminal of a second AND circuit 20. An output terminal O3 of the operation unit 14 provides $Z = |X - Y|$ to an input terminal of a comparator 21.

The other input terminal of the comparator 21 receives a set value V0, and the comparator 21 compares the value Z with the value V0. If $Z > V0$, the comparator 21 provides a high-level signal to an input terminal of a third AND circuit 22. The other input terminal of the third AND circuit 22 receives an inspection gate signal G. This gate signal G will be high when a boundary between the high- and low-brightness parts of the capsule c is scanned. An output of the third AND circuit 22 is provided to the other input terminal of the first AND circuit 19 as well as to the other input terminal of the second AND circuit 20.

An output of the first AND circuit 19 is provided to a set terminal S of a first flip-flop circuit 23 as well as to an input terminal of an OR circuit 24. An output of the second AND circuit 20 is provided to a reset terminal R of the first flip-flop circuit 23 as well as to the other input terminal of the OR circuit 24. An output of the OR circuit 24 is provided to a set terminal S of a second flip-flop circuit 25. A reset terminal R of the second flip-flop circuit 25 receives a horizontal scan synchronization reset signal H for the CCD line image sensors 5 and 6.

Outputs of the first and second flip-flop circuits 23 and 25 are provided to an exclusive OR circuit 26. An output of the exclusive OR circuit 26 is provided to an input terminal of a fourth AND circuit 27.

The operation unit 14, comparator 21, first AND circuit 19, second AND circuit 20, third AND circuit 22, first flip-flop circuit 23, OR circuit 24, second flip-flop circuit 25, exclusive OR circuit 26, and fourth AND circuit 27 form positional relation determination means for determining a positional relation between the high- and low-brightness parts of the capsule c.

The object kind presetting unit PS turns On a switch 28 when the object(capsule c) involves different colors and OFF when the object is monochrome. The switch 28 is connected in series with a constant voltage source Vcc. An output of the switch 28 on the constant voltage source Vcc side is passed through an inverter 29 and provided to the other input terminal of the fourth AND circuit 27.

An output of the fourth AND circuit 27 is provided to the output switching circuit 17. The output switching circuit 17 provides an image processing unit with the image signal A5 when the fourth AND circuit 27 provides a low-level output and the image signal B5 when the fourth AND circuit 27 provides a high-level output. The output switching circuit 17 forms image signal selection means.

The image signal provided by the output switching circuit 17 is processed by the image processing unit to inspect the surface conditions of the capsule c.

Operations of the embodiment will now be explained.

Figure 3:
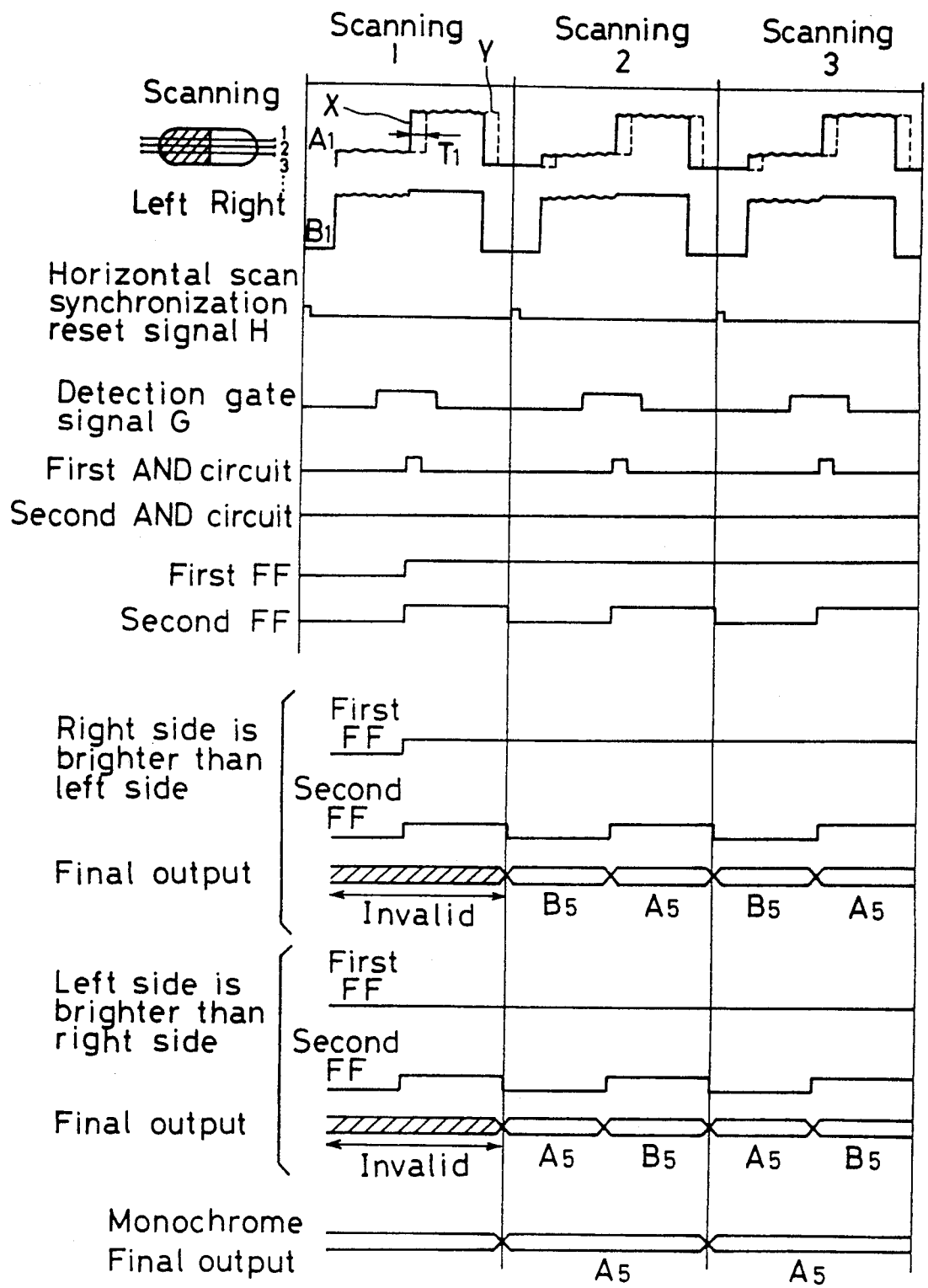
FIG. 3 is a time chart showing signal statuses of essential parts of the embodiment.

When a colored capsule c is transported to the image pick-up position with the right side (seen from a trailing end of transportation) of the capsule c being a high-brightness part (for example, colored white) and the left side of the capsule c being a low-brightness part (for example, colored red), processes shown in the flowchart of FIG. 2 and the time chart of FIG. 3 are carried out.

Step S1 turns ON the switch 28 through the object kind presetting unit PS and selects one of the filter segments in each of the high-brightness adjusting optical filter 4 and low-brightness adjusting optical filter 5 according to a brightness combination on the colored capsule c. For example, a dark red filter segment is selected for the optical filter 4, and a light red filter segment for the optical filter 5. As a result, the quantity of light reflected by the white part of the capsule c and transmitted through the optical filter 4 will be substantially equal to the quantity of light reflected by the red part of the capsule c and transmitted through the optical filter 5.

Light beams transmitted through the adjusted optical filters 4 and 5 are photoelectrically converted by the CCD line image sensors 6 and 7 into image signals A1 and B1. As shown in FIG. 3, the image signal A1 is formed with the right high-brightness part of the capsule c being set to a reference level, and the image signal B1 is formed with the left low-brightness part of the capsule c being set to the reference level and with the high-brightness part being saturated.

In step S2, the object kind presetting unit PS controls amplification factors of the amplifiers 8 and 9 so that output signal levels of the amplifiers 8 and 9 will be equal to each other once the quantity of light from the white part of the capsule transmitted through the optical filter 4 and the quantity of light from the red part of the capsule transmitted through the optical filter 5 are adjusted to the reference level.

In step S3, the low-pass filters 10 and 11 remove noise components from the amplified image signals A2 and B2 and provide image signals A3 and B3, respectively.

In step S4, the A/D converters 12 and 13 convert the signals A3 and B3 into digital image signals A4 and B4, respectively.

In step S5, the image signal A4 is supplied as is to the operation unit 14. At the same time, the image signal A4 is delayed by the delay circuit 15 by the predetermined time T1 and provided as a delayed signal A4' to the operation unit 14.

In step S6, a difference $|X - Y|$ between levels X and Y of the undelayed and delayed signals A4 and A4' is checked to see whether or not it is greater than the set value V0, to determine whether or not there is a predetermined brightness difference between the high- and low-brightness parts of the capsule c, i.e., whether the capsule c is colored with two colors or monochrome.

If the capsule c has the predetermined brightness difference, i.e., if it involves two colors, the detection gate signal G becomes high only around a boundary between the colored parts of the capsule c, and the comparator 21 will provide a high-level output. As a result, the third AND circuit 22 provides a high-level output.

If the capsule c is monochrome with no brightness difference, the comparator 21 provides a low-level output, and therefore, the third AND circuit 22 provides a low-level output.

Step S7 compares the level X of the undelayed signal A4 with the level Y of the delayed signal A4'. If the high-brightness part of the capsule c is on the right side in a scanning direction, the delayed signal A4' will be as indicated with a dotted line in FIG. 3. Namely, just after the boundary between the colored parts, X will be greater than Y, and after the predetermined time T1, X will be nearly equal to Y. As a result, the second AND circuit 20 provides a low-level output, and the output of the first AND circuit 19 rises to a high level at the boundary of the colored parts and falls to a low level after the predetermined time T1.

In this way, when the first AND circuit 19 provides a pulse, it is determined that the high-brightness part of the capsule c is on the right side.

On the other hand, if the high-brightness part of the capsule c is on the left side, X will be smaller than Y just after the boundary of the colored parts, and X will be nearly equal to Y after the predetermined time T1. In this case, the output of the first AND circuit 19 is maintained at low level, and the output of the second AND circuit 20 rises to a high level at the boundary of the colored parts and falls to a low level after the predetermined time T1.

When the high-brightness part of the capsule c is on the right side, the output of the first AND circuit 19 rises to set the first flip-flop circuit 23, which then provides a high-level output. The OR circuit 24 provides a high-level output because the output of the first AND circuit 19 becomes high. As a result, the second flip-flop circuit 25 is set and provides a high-level output. Since the output level of the first flip-flop circuit 23 is equal to that of the second flip-flop circuit 25, the exclusive OR circuit 26 provides a low-level output, and the fourth AND circuit 27 also provides a low-level output.

For the first horizontal scanning after the start of scanning, the image signals A1 and B1 are provided as signals A5 and B5 to the output switching circuit 17 after being delayed by the delay circuits 16 and 18 by the predetermined time T2 corresponding to one horizontal scanning period, so that the output switching circuit 17 is switched to a given side before the start of scanning.

Namely, the first flip-flop 23 determines whether the high-brightness part is on the right or left side of the capsule c according to characteristic parts of the image signals and holds this determination until the characteristic parts of the next scanning arrive there.

The second flip-flop 25 is reset by the horizontal scan synchronization reset signal H just before starting horizontal scanning, and provides a low-level output. When the image signals are changed by a predetermined level, i.e., when a scanned part is switched between the high- and low-brightness parts, the output of the second flip-flop 25 rises to a high level. This provides timing for switching the two image signals from one to another.

When the output of the second flip-flop 25 rises, the output levels of the first and second flip-flop circuits 23 and 25 becomes equal to each other, so that the exclusive OR circuit 26 provides a low-level output to one input terminal of the fourth AND circuit 27. At this moment, the switch 28 is ON and the inverter 29 provides a high-level output to the other input terminal of the fourth AND circuit 27, so that the fourth AND circuit 27 provides a low-level output. As a result, the output switching circuit 17 provides the signal A5 formed from the signal A1 and delayed by the predetermined time T2, to the image processing unit.

In the next stage, the output switching circuit 17 provides the signal B5 formed from the image signal B1 and delayed by the predetermined time T2 until the second flip-flop circuit 25 again provides a high-level output at the boundary of the colored parts of the capsule c, so that the exclusive OR circuit 26 and fourth AND circuit 27 provide each a low-level output. From this moment until the horizontal scan synchronization reset signal H is received, the output switching circuit 17 again selects the image signal A5.

In this way, from the second horizontal scanning, the image signal B5 based on the low brightness side is selected in response to the horizontal scan synchronization reset signal H up to the boundary of the colored parts, and the image signal A5 based on the high-brightness side is selected from the boundary up to the next synchronization signal H.

Step S10 repeats these operations. Namely, the step S10 provides, for the low-brightness part on the left side of the capsule c, the image signal B5 with transmitted light from the low-brightness part being adjusted to a reference level, and for the high-brightness part on the right side of the capsule c, the image signal A5 with transmitted light from the high-brightness part being adjusted to the reference level. As a result, the image signal adjusted to the reference level is provided to the image processing unit for the whole period of scanning, to accurately inspect the surface conditions of the capsule c.

If the high-brightness part of the capsule is on the left side and the low-brightness part on the right side, the first AND circuit 19 and first flip-flop circuit 23 will be each kept at a low level, and the second flip-flop circuit 23 will be changed to a high level at the boundary of the colored parts similar to the previous case. Accordingly, the exclusive OR circuit 26 and fourth AND circuit 27 provide each a low-level output in the first half of horizontal scanning and a high-level output in the second half thereof. As a result, the output switching circuit 17 selects the high-brightness side adjusted image signal A5 for the first half of the horizontal scanning, and the low-brightness side adjusted image signal B5 for the second half.

Step S11 repeats these operations. Namely, the step S11 provides the image signal adjusted to the reference level to the image processing unit for the whole period of scanning, to accurately inspect the surface conditions of the capsule c.

With this arrangement, a signal level for the high-brightness part of the medical capsule c and that for the low-brightness part of the capsule are adjusted to the reference level by properly setting the transmission wavelength ranges of the optical filters 4 and 5. Unlike the prior art that adjusts signal levels by amplification, the invention never amplifies noise components to cause errors in inspection. The invention thus improves inspection accuracy. Since level adjustments made by the amplifiers 8 and 9 of the invention are very fine, it will never amplify noise components to an influencing extent.

When the surface of a medical capsule to be inspected is monochrome with no color difference, the object kind presetting unit PS selects one of the filter segments of the optical filter on the high-brightness adjusting side, adjusts the amplification factor of the amplifier 8, and turns OFF the switch 28. In this case, the fourth AND circuit 27 always provides a low-level output so that the output switching circuit 17 always provides the high-brightness adjusted side image signal A5 to the image processing unit, which properly inspects the surface conditions of the capsule.

Since the stages following the A/D converters 12 and 13 handle digital signals, microcomputers may be employed to process the signals with software.

The embodiment selects and provides one of two signals. These two signals, which belong to temporally different ranges, may be transferred as they are in parallel to latter stages, and switched from one to another during operation.

We claim:

1. A method of picking up an image of the surface of an object to be inspected, comprising:
    a light dividing step of dividing light reflected by the object surface into two parts oriented in two different directions;
    a transmitted light quantity adjusting step of transmitting each of the divided parts of the light through an optical filter set to a specific transmission light wavelength range, to adjust the quantity of light reflected by a high-brightness part of the object surface and transmitted through one of the optical filters and the quantity of light reflected by a low-brightness part of the object surface and transmitted through the other optical filter to the same reference level; and
    an image pick-up step of picking up an image from each of the two parts of the light transmitted through the optical filters.

2. A method according to claim 1, wherein the filtering face of each of the optical filters comprises a plurality of filter segments having different transmission light wavelength ranges, and the transmitted light quantity adjusting step transmits each of the divided parts of the light through one of the filter segments that has been selected according to a brightness combination on the object surface.

3. A method of inspecting the surface of an object, comprising:
    a delay step of delaying one image signal that has been formed by setting the quantity of transmitted light from a high-brightness part of the object to a reference level, one of two image signals prepared by the method of claim 1; and
    a positional relation determination step of comparing the delayed image signal with the undelayed image signal, to determine a positional relation between the high-and low-brightness parts of the object.

4. A method according to claim 3, further comprising an image signal selection step of switching the two image signals from one to another according to a timing signal generated according to the positional relation determined by the positional relation determination step, to provide an image processing unit with the signal prepared by setting the quantity of transmitted light from the high- or low-brightness part to the reference level.

5. A method according to claim 3, wherein the positional relation determination step has a function of providing the image processing unit only with the image signal prepared by setting the quantity of transmitted light from the high-brightness part to the reference level, if the positional relation determination step determines that the object surface involves no brightness difference.

6. An apparatus for picking up an image of the surface of an object to be inspected, comprising:
    light dividing means for dividing light reflected by the object surface into two parts oriented in two different directions;
    transmitted light quantity adjusting means for transmitting each of the divided parts of the light through an optical filter set to a specific transmission light wavelength range, to adjust the quantity of light reflected by a high-brightness part of the object surface and transmitted through one of the optical filters and the quantity of light reflected by a low-brightness part of the object surface and transmitted through the other optical filter to the same reference level; and
    image pick-up means for picking up an image from each of the two parts of the light transmitted through the optical filters.

7. An apparatus according to claim 6, wherein the filtering face of each of the optical filters of the transmitted light quantity adjusting means comprises a plurality of filter segments having different transmission light wavelength ranges, and in each of the optical filters, one of the filter segments is selected according to a brightness combination on the object surface.

8. An apparatus for inspecting the surface of an object, comprising:
    delay means for delaying one image signal that has been formed by setting the quantity of transmitted light from a high-brightness part of the object to a reference level, out of two image signals prepared by the image pick-up means of the apparatus of claim 6; and
    positional relation determination means for comparing the delayed image signal with the undelayed image signal, to determine a positional relation between the high- and low-brightness parts of the object.

9. An apparatus according to claim 8, further comprising image signal selection means for switching the two image signals from one to another according to a timing signal generated according to the positional relation determined by the positional relation determination means, to provide an image processing unit with the signal prepared by setting the quantity of transmitted light from the high- or low-brightness part to the reference level.

10. An apparatus according to claim 8, wherein the positional relation determination means has a junction of providing the image processing unit only with the image signal prepared by setting the quantity of transmitted light from the high-brightness part to the reference level, if the positional relation determination means determines that the object surface involves no brightness difference.

* * * * *